United States Patent
Watson et al.

(10) Patent No.: US 10,788,890 B1
(45) Date of Patent: Sep. 29, 2020

(54) CLOSED-LOOP SYSTEM FOR INFLUENCING MENTAL/EMOTIONAL STATE WITH IMMERSIVE SENSORY SURROUNDINGS

(71) Applicant: X Development LLC, Mountain View, CA (US)

(72) Inventors: Philip Watson, Felton, CA (US); Christian Ervin, Burlingame, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 16/365,095

(22) Filed: Mar. 26, 2019

(51) Int. Cl.
| | |
|---|---|
| G06F 3/01 | (2006.01) |
| A61M 21/02 | (2006.01) |
| A61B 5/00 | (2006.01) |
| G16H 20/70 | (2018.01) |
| A61M 21/00 | (2006.01) |

(52) U.S. Cl.
CPC ............ *G06F 3/011* (2013.01); *A61B 5/0015* (2013.01); *A61B 5/486* (2013.01); *A61M 21/02* (2013.01); *G16H 20/70* (2018.01); *A61B 5/0006* (2013.01); *A61M 2021/005* (2013.01); *A61M 2021/0027* (2013.01); *G06F 2203/011* (2013.01)

(58) Field of Classification Search
CPC .... G06F 3/011; G06F 2203/011; A61B 5/486; A61B 5/0015; A61B 5/006; A61M 21/02; A61M 2021/0027; A61M 2021/005; G16H 20/70
See application file for complete search history.

(56) References Cited

U.S. PATENT DOCUMENTS 8,874,511 B1 * 10/2014 Mathias ................. G06F 16/27
                                                            707/620
9,612,654 B2    4/2017 Brokken et al.
(Continued)

FOREIGN PATENT DOCUMENTS

EP         2997887 A1      3/2016

OTHER PUBLICATIONS

Ajay BS, "Emotion Detection Using Machine Learning", International Journal of Recent Trends in Engineering and Research, vol. 3, Issue 6, Jun. 2017, 5 pages.
(Continued)

*Primary Examiner* — Liliana Cerullo
(74) *Attorney, Agent, or Firm* — Christensen O'Connor Johnson Kindness PLLC

(57) ABSTRACT

A technique for encouraging a user towards a selected mental or emotional state includes: determining an influencing directive for encouraging the user towards the selected mental or emotional state; selecting environmental content, based upon the influencing directive, from a plurality of different types of environmental content; presenting the environmental content to the user via sensory immersion equipment, wherein the includes at least one environmental display for altering an ambience of a room; generating observation data based upon observing a user reaction to the environmental content with an observation system, the observation system including at least one sensor capable of observing the user reaction; and determining whether to adjust the environmental content based upon the observation data to encourage the user towards the selected mental or emotional state.

19 Claims, 4 Drawing Sheets

(56) References Cited

U.S. PATENT DOCUMENTS

| | | | |
|---|---|---|---|
| 2014/0247155 A1* | 9/2014 | Proud | A61B 5/02055 340/870.16 |
| 2015/0199010 A1* | 7/2015 | Coleman | A61B 5/0006 345/156 |
| 2015/0294595 A1 | 10/2015 | Hu et al. | |
| 2016/0247083 A1 | 8/2016 | Adoni et al. | |
| 2018/0246570 A1 | 8/2018 | Coleman et al. | |
| 2019/0034706 A1 | 1/2019 | el Kaliouby et al. | |

OTHER PUBLICATIONS

"Mental Health & Function: How the Experience of Nature Aids the Brain", University of Washington, Datasheet No. 5 of 13, Dec. 2012, 1 page.

Goodyear, S., "Green Spaces That Actually Calm the Mind and Body", Citylab, Jun. 26, 2013, 5 pages.

Delistraty, C., "How Environment Can Boost Creativity", The Atlantic, Sep. 14, 2014, 4 pages.

Houlden, V. et al., "The Relationship Between Greenspace and the Mental Wellbeing of Adults: A Systematic Review", PLOS One, Sep. 12, 2018, 35 pages.

Tellart, "Our Future Life with Intelligent Machines", Retrieved from the internet on Mar. 14, 2019: <https://www.tellart.com/projects/museum-of-the-future-machinic-life/index.html>, Dubai Future Foundation, 20 pages.

Cooper, B., "The Science Behind Your Ideal Work Environment", Fastcompany.com, Jan. 11, 2019, 7 pages.

\* cited by examiner

US 10,788,890 B1

CLOSED-LOOP SYSTEM FOR INFLUENCING MENTAL/EMOTIONAL STATE WITH IMMERSIVE SENSORY SURROUNDINGS

TECHNICAL FIELD

This disclosure relates generally to systems that influence mental/emotional state based upon sensory surroundings.

BACKGROUND INFORMATION

It is well documented that an individual's environment can influence their mental/emotional state. For example, researchers have explored how environment can boost creativity, weather affects mood, green spaces impact mental health, and so on. While the fact that our surroundings can have significant impact on our mental and/or emotional state is widely accepted, how to effectively leverage this knowledge to beneficially influence mental and/or emotional state is not.

Conventional approaches to influencing mental health typically propose having individuals physically alter/change their environments to achieve a desired outcome. However, this can be a burdensome approach to optimizing mental/emotional state, and not easily customizable. There are certain environmental trends that hold true across large populations of people (e.g., color to paint hospital walls to have a calming influence, etc.); however, there are many environmental influencers that may be culturally based or even individualistic. Conventional approaches are not well suited to identifying and implement individualistic approaches to beneficially altering one's environment in a dynamic way.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
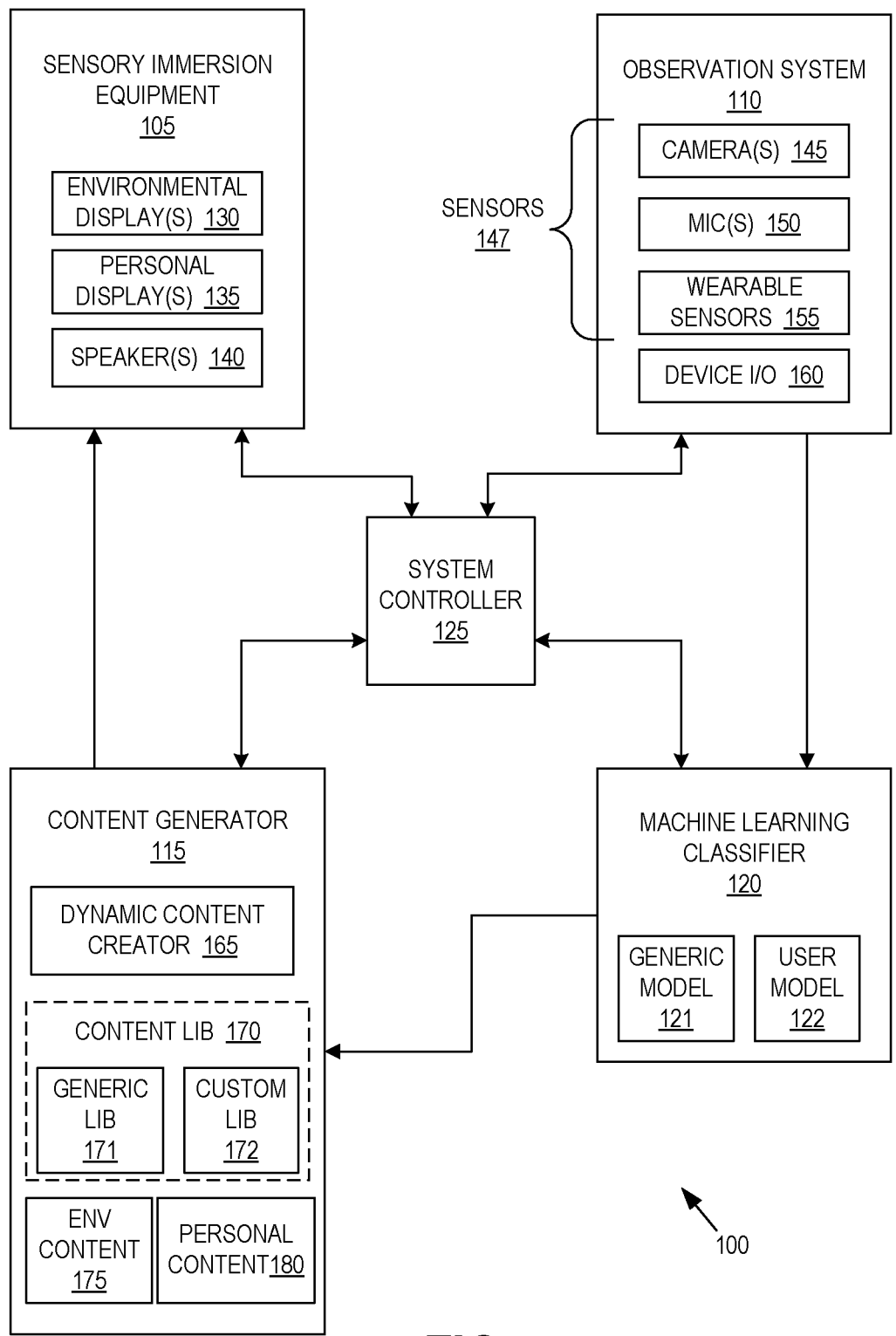
FIG. 1 is a functional block diagram illustrating components of a user encouragement system, in accordance with an embodiment of the disclosure.

Embodiments of a system, apparatus, and method of operation of a user encouragement system for encouraging users toward selected mental or emotional states are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Tools exist to create immersive environments in a dynamic way, observe a person to extract mental/emotional state from that person, and even evaluate the operational effectiveness of how a person is doing while performing a particular activity. Accordingly, embodiments of the present disclosure describe a user encouragement system that combines these tools in a closed-loop experimental manner to generate environmental content that alters the ambience of an immersive environment, observes an individual's mental/emotional state in response to presentation of the environmental content, and then learns what content effectively leads or encourages an individual towards a desired mental/emotional state. In one embodiment, the content deemed effective for a given user may be determined via application of a machine learning (ML) algorithm or ML classifier. This closed-loop system may then be applied to help a user achieve desired mental/emotional states (e.g., creative state, focused state, relaxed state, calming state, excited state, etc.) to productive ends.

The user encouragement system may also be applied to identify or determine an influencing directive for encouraging the user towards a selected mental or emotional state. In one embodiment, the influencing directive may be explicitly determined by receiving an explicit directive. For example, an explicit directive may be an explicit request from the user to present environmental content that will help the user achieve their desired mental/emotional state (e.g., be creative, relax, focus, etc.). Alternatively, the influencing directive may be implicitly determined by observing activities performed by the user, identifying those activities, and associating a mental/emotional state that is conducive to the user accomplishing the identified activity. The system may then automatically present environmental content that it has learned helps the user achieve the determined mental/emotional state. For example, the user encouragement system may determine that the user is writing a letter by observing the user and/or observing input/output (I/O) of connected devices (personal or desktop computing device). Once an activity or task has been identified, the user encouragement system may then determine that the influencing directive is creativity and/or a focused mental state, and thus present environmental content that the system has learned tends to help the individual achieve a creative or focused mental/emotional state.

The environmental content selected to implement a determined influencing directive may be selected from a catalog or library of stored content that is generic or customized for the user. Alternatively (or additionally), the environmental content may be dynamically generated. The environmental content may be presented to the user via connected sensory immersion equipment. Sensory immersion equipment is broadly defined herein to include equipment capable of immersing or filling a significant portion of a given sense and thus altering the ambience of a room in a meaningful way for that user. In the example of vision or sight, a display that fills a meaningful portion of the user's vision may be used. In one embodiment, a display that fills approximately a 110 degrees of vision (or more) may be used, though embodiments described herein are not so limited. The sensory immersion equipment may be expanded to influence other senses than just sight, such as hearing, touch, smell, or taste.

In some embodiments, the environmental content may be altered in connection with alterations to personalized content viewed on personal screens (e.g., mobile computing device, desktop device, etc.). Thus, the visual/audible experience (e.g., background themes, font themes, color themes, audible themes, etc.) of application software executing on a personal device upon which most of the user's attention is focused may be altered in conformity with adjustments to environmental content affecting the room. This cross-platform thematic approach may heighten the immersive effects and overall effectiveness of the user encouragement system.

FIG. 1 is a functional block diagram illustrating components of a user encouragement system 100, in accordance with an embodiment of the disclosure. The illustrated embodiment of system 100 includes sensory immersion equipment 105, observation system 110, a content generator 115, a machine learning (ML) classifier (or ML algorithm) 120, and a system controller 125. The illustrated embodiment of sensory immersion equipment 105 includes environmental display(s) 130, personal displays 135, and speakers 140. The illustrated embodiment of observation system 110 includes camera(s) 145, microphone(s) 150, wearable sensor(s) 155, and device inputs/outputs (I/Os) 160. Generically, camera 145, microphone 150, and wearable sensor 155 are referred to as sensors 147. The illustrated embodiment of content generator 115 includes a dynamic content creator 165, a content library 170, environmental content 175, and personal content 180. Content library 170 may include generic library 171 and custom library 172. The illustrated embodiment of ML classifier 120 includes a generic model 121 and a user model 122.

Sensory immersion equipment 105 represents communicatively connected equipment that is controlled by system controller 125 to generate an immersive environment capable of altering the ambience of a room (e.g., an office, a cubical space, a work space, a conference room, an exercise room, a kitchen, a family room, etc.) and thereby influencing the mental or emotional state of the occupants of that room. Sensory immersion equipment 105 may include a variety of equipment capable of substantially immersing a given sense, including sight, sound, smell, touch, or taste. However, equipment capable of affecting the senses of sight and sound is expected to be the primary influencing equipment. For example, environmental displays 130 may include one or more display panels, a tiled array of display panels, projector equipment, wallpaper-like displays disposed on walls and/or table surfaces, etc. Environmental display(s) 130 represents displays positioned in the room for general viewing by one or more occupants of the room and are intended to influence the overall room ambience via the presentation of environmental content. In one embodiment, environmental displays include display equipment capable of filling at least a 110 degree field of view (FOV) of a user within the room. In contrast, personal displays 135 are intended to represent the displays of personal or desktop computing devices typically used by a single user at a time for personal entertainment or individual productivity use. Personal displays 135 are typically fixated upon during use and thus the thematic presentation of the personal content displayed on such devices may also have a significant impact on an individual's mental/emotional state, even if the personal displays don't full immerse a 110 degrees of the user's FOV. However, personal displays 135 may also represent individual virtual reality or augmented reality displays (e.g., head wearable displays). Speakers 140 may represent general audio speakers such as wall speakers, floor speakers, desktop speakers, headphones, earbuds, or otherwise.

The illustrated embodiment of observation system 110 includes one or more sensors 147 for observing the user and a user reaction to presentation of the environmental content by sensory immersion equipment 105. In the illustrated embodiment, observation system 110 is communicatively connected to at least system controller 125, and potentially other system components (e.g., ML classifier 120), to provide observation data generated based upon the user reaction. Sensors 147 may include one or more cameras 145, such as wall/ceiling mounted cameras (or video cameras), cameras integrated into a personal computing device, desktop camera, monitor mounted camera, etc. Similar, microphone 150 may be integrated into a personal computing device, a standalone microphone, or otherwise. Wearable sensors 155 may represent any wearable device capable of measuring, monitoring, or acquiring one or more of a body temperature, a pulse rate, an electrocardiogram (ECG), or other body status indicators. An example wearable device may include a wrist watch with integrated sensors.

Device I/O 160 represents the I/O of personal or desktop computing devices operated by the user. For example, the keystrokes on a keyboard may be monitored as indicia of mental/emotional state (e.g., is the user typing in a bursty, erratic manner, a calm steady manner, mashing keys, etc.). Of course, device I/O 160 may also represent the content generated by the user and input or output from applications the user is utilizing or accessing. As an example, the identification that a user is writing a letter with a text editor, coding with a software development tool, writing email, designing with a CAD tool, or otherwise may be determined from the I/O of a computing device and/or the applications executing on the computing device, and thus this information is also generically included within the definition of the term device I/O 160.

ML classifier 120 may be implemented as a machine learning algorithm communicatively coupled to receive observation data from observation system 110 and make decisions as to what environmental content is likely to encourage the user towards a selected mental or emotional state. In one embodiment, ML classifier 120 is a generative neural network trained on different types of scenery, patterns, or other audio/visual (A/V) stimuli along with the observation data of how that A/V stimuli influenced the user. In one embodiment, ML classifier 120 operates with a generic model 121 that has been trained on a large data sample. In one embodiment, ML classifier 120 implements a reinforcement learning algorithm that adapts and continues to learn. For example, the reinforcement learning algorithm may begin with the generic model 121, but update and refine generic model 121 based upon interactions with a given user to generate a continually refined user model 122. Accordingly, user model 122 may be continually updated based upon user reactions observed in response to presentation of selected environmental content with sensory immersion equipment 105. In one embodiment, ML classifier 120 selects and presents environmental content (via sensory immersion equipment 105) to test the user and refine user model 122. In some instances, the user is not explicitly informed and thus may not be aware that the environmental content being presented is a test to refine user model 122. In other embodiments, the ML classifier 120 monitors explicit requests made by a given user while the user is performing a given task and uses this data to further refine user model 122. Associations between a desired mental/emotional state, the optimal content to encourage a user towards that mental/emotional state, and the activities performed by a given user may be learned from observing user requests for certain environmental content while the user is performing a particular activity.

In addition to generating and refining user model 122, ML classifier 120 may also be operated to learn how to determine implicit directives for influencing the user towards a selected mental or emotional state by identifying a task or activity being performed by the user. In other words, ML classifier 120 may received observation data from observation system 110 from which the task/activity (e.g., writing, coding, designing, etc.) being performed may be determined. Once the task/activity is determined the ML classifier 120 may be used to associate that task/activity with optimal environmental content that is conducive to the user accomplishing the particular task/activity. This may be akin to determining a mental or emotional state that is conducive to accomplishing the identified task, then selecting environmental content associated with encouraging or stimulating that mental or emotional state.

Content generator 115 is a module that creates or otherwise provides the environmental content displayed on sensory immersion equipment 105. Content generator 115 may include a content library 170 of pre-generated content or a dynamic content creator 165 capable of generating new content in real-time. Content library 170 may include generic library 171 including content that is generally applicable and otherwise curated for large classes of people (e.g., generic content for males, for females, for age groups, for certain cultural groups, for certain interest/hobby groups, etc.). Content library 170 may also include a custom library 172 that includes environmental content that has been curated for a given user based upon previous interactions and feedback from ML classifier 120. In one embodiment, the content stored in or created by content generator 115 may be further categorized into environmental content 175 for displaying on environmental display(s) 130 and personal content 180 for displaying on personal display(s) 135. Instances of environmental content 175 may be linked to instances of personal content 180 and collectively correlated to particular influencing directives. For example, environmental content 175 and personal content 180 may be thematic images, colors, fonts, sounds, music, etc.

Finally, system controller 125 is communicatively coupled to each of the other components within system 100 and operates to choreograph their operation. In one embodiment, system controller 125 is responsible to identifying activities performed by the user and associating those activities with an influencing directive. In some embodiments, the identification of activities and association of those activities with an influencing directive (e.g., help user be creative, help user calm down, help user focus, etc.) may be performed in cooperation with ML classifier 120. System controller 125 may also be responsible for determining when ML classifier 120 may present test content to the user, or be the portal through which the user is able to make explicit requests for particular influencing help. In other words, the user may be capable of submitting an explicit directive via system controller 125 to present environmental content that will foster creativity or otherwise.

System controller 125 may include centralized logic stored in a memory module and executed by a microprocessor. Alternatively, system controller 125 may include decentralized logic that is stored across the various other components of system 100. System controller 125, ML classifier 120, and content generator 115 may be implemented entirely in software or implemented as a combination of hardware and software logic.

Figure 2:
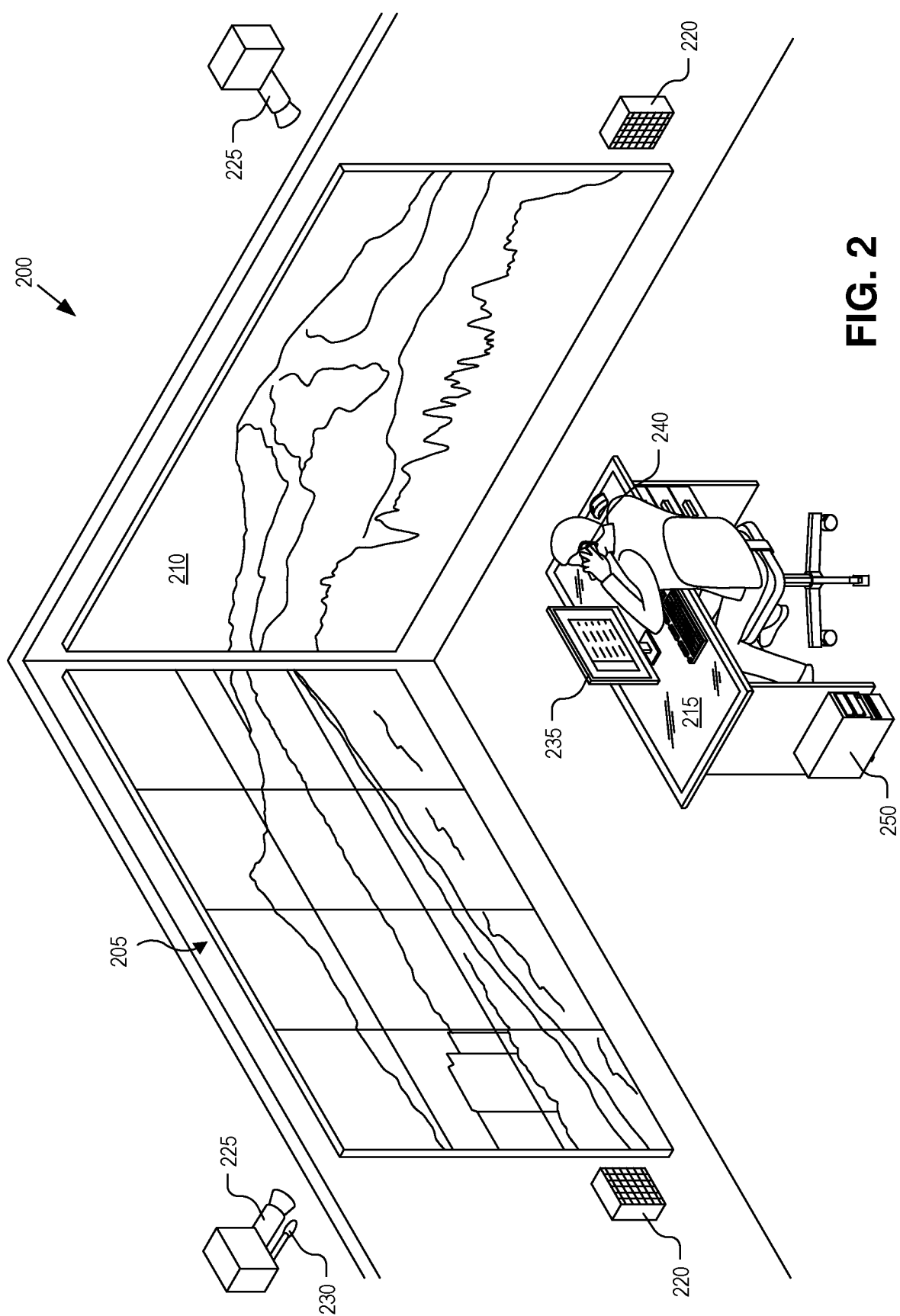
FIG. 2 is a perspective view illustration of a sensor immersive environment, in accordance with an embodiment of the disclosure.

FIG. 2 is perspective view illustration of sensor immersive environment 200, in accordance with embodiments of the disclosure. Environment 200 is one possible environment into which user encouragement system 100 may be deployed. In environment 200, sensory immersion equipment 105 may be implemented with a tiled array of display panels 205, a large wallpaper-like or panel display 210, and a tabletop surface display 215 (all corresponding to environmental displays 130) while speakers 220 may be mounted to the walls (or otherwise) to provide audible immersion. By providing displays throughout the room, the user's vision is immersed. Observation system 110 may be implemented with cameras 225 and microphone 230. Of course, the cameras and microphones may be integrated into the user's desktop monitor 235 and/or mobile computing device 240. Content generator 115, ML classifier 120, and system controller 125 may be executed on computer 250 and/or distributed to cloud computing resources communicatively coupled to computer 250 via a network.

FIG. 2 illustrates environmental displays 205 and 210 on different walls. In some embodiments, displays on opposing walls may be controlled by system controller 125 to influence different users in the same room with different environmental content according to their personalized needs/desires. Accordingly, influencing content can be created and the ambience of a room adjusted to influence multiple occupants with different viewing angles towards different mental/emotional states, or even a common mental/emotional state, but using customized content for each user.

Figure 3:
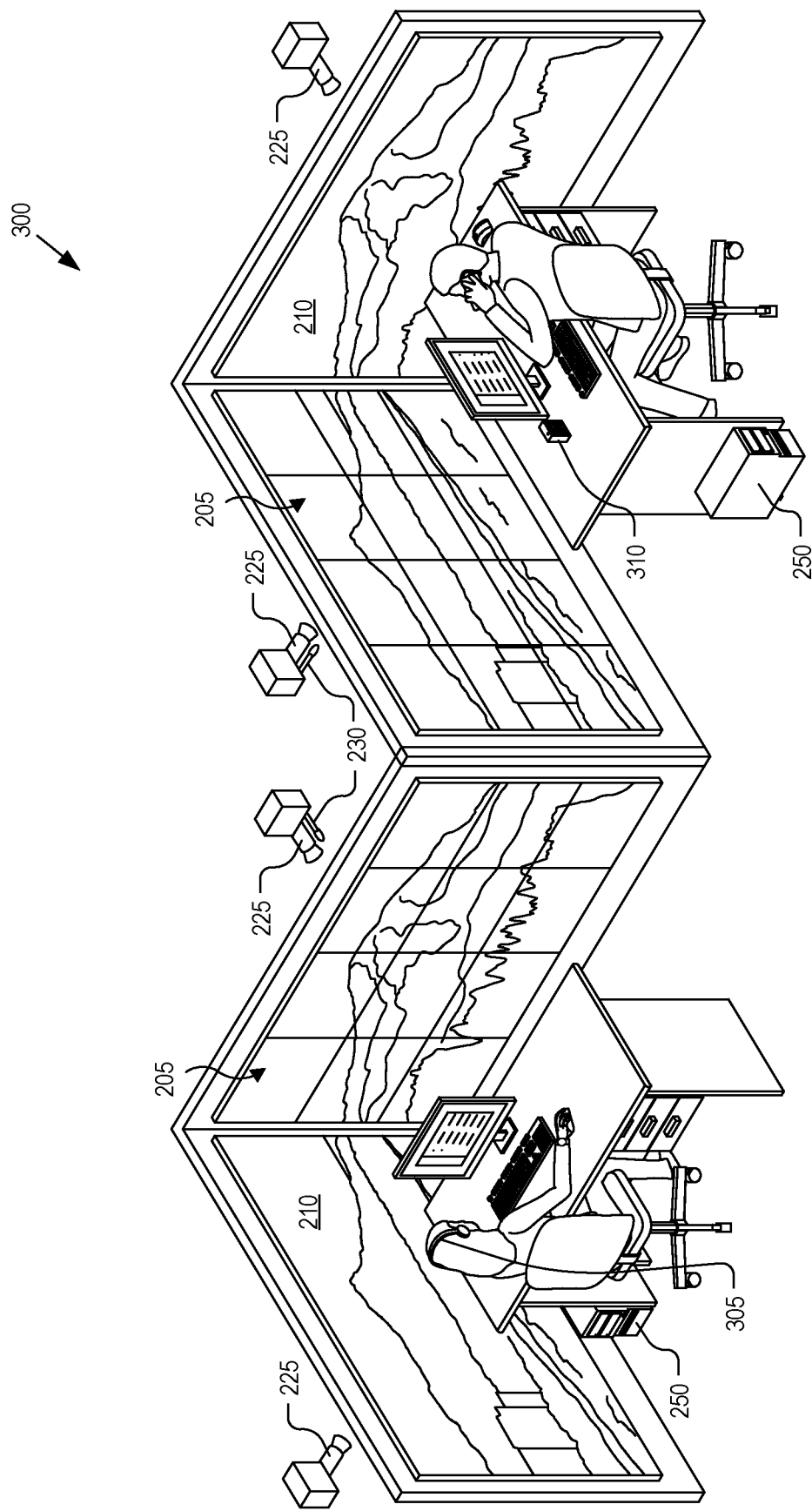
FIG. 3 is a perspective view illustration of a sensor immersive environment, in accordance with another embodiment of the disclosure.

FIG. 3 is a perspective view illustration of yet another sensor immersive environment 300, in accordance with another embodiment of the disclosure. Environment 300 is similar to environment 200, but illustrates how the sensory immersion equipment 105 and observation system 110 may be deployed in a cubical environment. Wall mount speakers 220 may be replaced with headphones 305 or desktop speakers 310 while the environmental displays (e.g., 205 or 210) line the cubical walls. Directional microphones 230 may be used, or rather desktop microphones (not illustrated) may be used. Though not illustrated, desktop surface displays (e.g., display 215) may also be deployed in environment 300.

Figure 4:
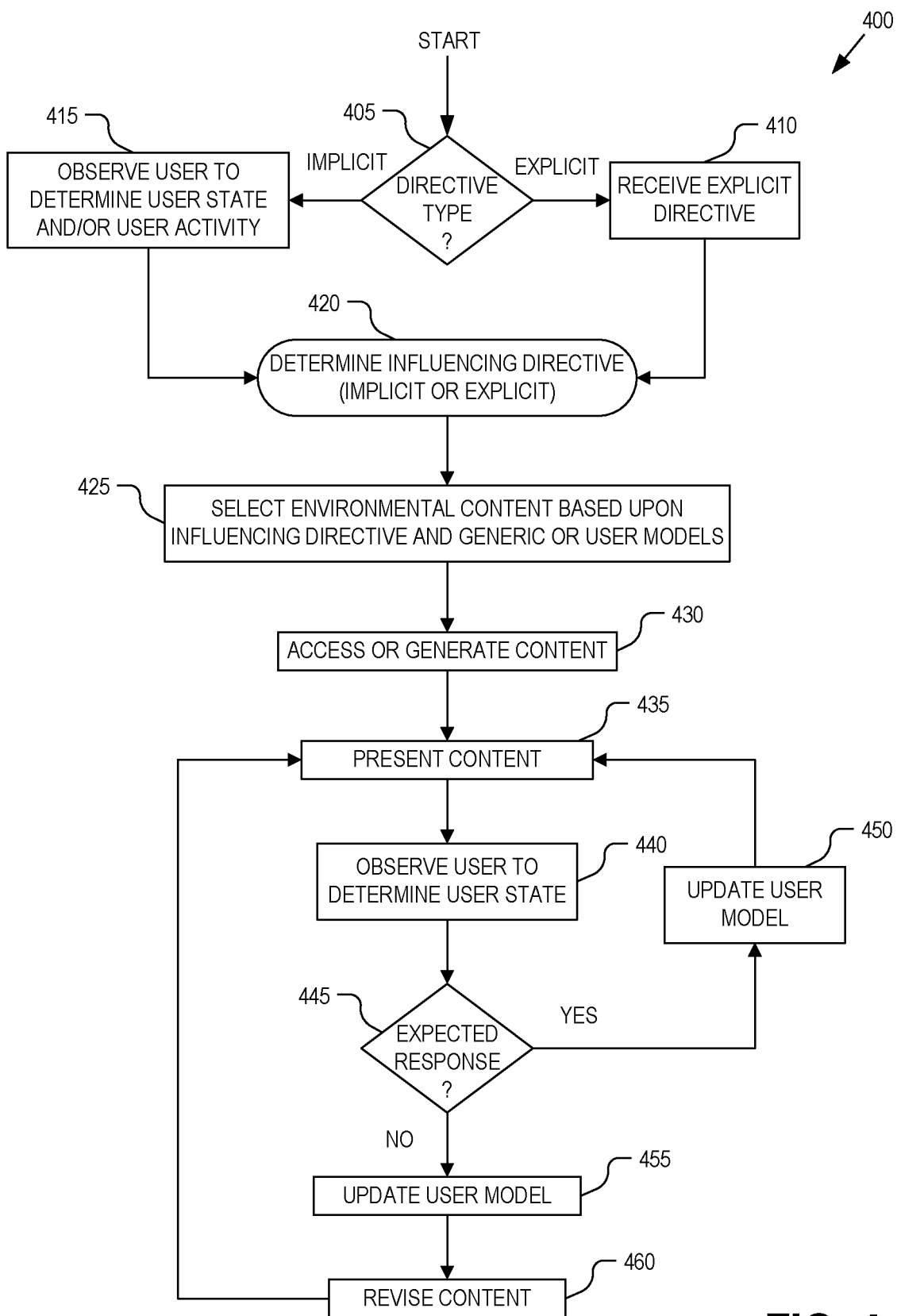
FIG. 4 is a flow chart illustrating operation of a user encouragement system for encouraging a user towards a selected mental or emotional state, in accordance with an embodiment of the disclosure.

FIG. 4 is a flow chart illustrating a process 400 of operation of user encouragement system 100 to encourage a user towards a selected mental or emotional state, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

Before influencing a user, an influencing directive needs to be determined (process block 420). The influencing directive is a determination or selection of what mental or emotional state the user should be encouraged towards. In other words, the influencing directive is a directive to help the user achieve a particular mental or emotional state. For example, an influencing directive may be a directive to influence the user towards calmness, creativity, focus, etc. However, the influencing directive may be determined as an explicit directive or an implicit directive (decision block 405). In the event of an explicit directive, system controller 125 receives the explicit directive from an external source (process block 410). The explicit directive may come from the user as an explicit request for help achieving a selected mental/emotional state or as a request for a particular environmental content. Alternatively, the explicit request may come from other external sources.

In the event of an implicit directive, system controller 125 seeks to implicitly determine a mental/emotional state that would help the user accomplish a particular task or activity by observing the user with observation system 110. Accordingly, in a process block 415, system controller 125 uses observation data output from observation system 110 to monitor the activity or activities being performed by the user, identify those activities, and then determine a selected mental or emotional state that is conducive to the user accomplishing those activities. In one embodiment, system controller 125 may employ ML classifier 120 to aid in identifying the user's activities based upon the observation data. In yet another embodiment, ML classifier 120 may even help with determining mental or emotional states that are conducive to the user accomplishing the identified activities. The identification of the activities may be executed based upon image data captured with camera 145, audio data captured by microphone 150, analyzing device I/O 160 from a personal computing device used by the user, or any combination thereof.

With an influencing directive determined, process 400 continues to a processing block 425 where environmental content is selected. The environmental content is content to be displayed on environmental displays 130 for influencing the ambience of a room in a manner that is consistent with the influencing directive. In one embodiment, ML classifier 120 selects the particular environmental content based upon the particular influencing directive and/or based directly or indirectly on the observation data. As mentioned above, ML classifier 120 may be a generic model 121 trained on a generic dataset that is generally applicable across one or more population segments that would include the user (e.g., based upon gender, culture, age, occupation, hobbies, interests, etc.). Alternatively, ML classifier 120 may be a user model 122 that was initially trained on generic datasets, but has been refined and updated based upon interactions with a particular user. For example, reinforced learning may be employed to generated and customize user model 122.

Once ML classifier 120 has identified and selected the particular content to be presented, content generator 115 may be used to either dynamically generate the requested content with dynamic content creator 165 or access the content from content library 170. In one embodiment, only environment content 175 for display on environmental display 130 is accessed or generated. In other embodiments, both environmental content 175 and personal content 180 is accesses and/or generated. In the scenario where the user is also using a personal display for a personal or desktop computing device, personal content 180 is related content (e.g., thematic content) that conforms to or otherwise buttresses environmental content 175. This related content may then be used to adjust visual themes (e.g., background colors, patterns, fonts, alert sounds, etc.) of applications executing on the user's personal display to further the influencing goals associated with the selected environmental content 175.

In a process block 435, the selected environmental content 175 and/or personal content 180 is presented to the user via sensory immersion equipment 105. While presenting the content to the user, system controller 125 operates observation system 110 to observe the user reaction to the content and generate further observation data indicative of the user reaction (process block 440). Again, this further observation data may be based upon image data, audio data, wearable sensor data, and/or device I/O data. In process block 445, system controller 125 may operate ML classifier 120 to analyze the observation data to determine whether the user response was the expected response based upon the user model 122 (decision block 445). As previously described, this analysis may use a machine learning algorithm to analyze facial expressions, pulse rate, breathing, blood pressure, pupil dilation, ECG, body temperature, typing rhythms, posture, or any number of observable reactions that may be correlated to a mental or emotional state. In alternative embodiments, system controller 125 may alternatively (or additionally) use non-ML algorithms or heuristic to analyze and categorize the user response.

If the expected user response was achieved, user model 122 may be updated as part of a reinforcement learning model (process block 450) and the selected content continues to be presented to the user in process block 435. However, if the user reaction is not deemed to be the expected or desired response (decision block 445), then process 400 continues to a process block 455 where user model 122 is again updated and revised content (e.g., environmental content 175 and/or personal content 180) is selected by ML classifier 120 (process block 460) for presentation in process block 435.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A user encouragement system, comprising:
sensory immersion equipment that alters an ambience of a room, the sensory immersion equipment including at least one environmental display and a personal display for a personal or desktop computing device, wherein the at least one environmental display includes an electronic display viewable from within the room, larger than the personal display, and which fills at least 110 degrees of vision of a user within the room;
an observation system including at least one sensor capable of observing the user in the room; and
a controller coupled to coordinate operation of the sensory immersion equipment and the observation system, the controller including logic that when executed causes the user encouragement system to perform operations including:
determining an influencing directive, wherein determining the influencing directive includes:
monitoring one or more activities performed by the user with the observation system;
identifying the one or more activities with a machine learning classifier; and
determining a selected mental or emotional state that is conducive to the user accomplishing the one or more activities identified by the machine learning classifier;
selecting environmental content, based upon the influencing directive, from a plurality of different types of environmental content;
presenting the environmental content to the user via the sensory immersion equipment;
adjusting a first theme of an application displayed on the personal display to conform with a second theme displayed on the environmental display;
generating observation data based upon observing a user reaction to the environmental content with the observation system; and
determining whether to adjust the environmental content based upon the observation data with a goal of advancing the user towards the selected mental or emotional state.

2. The user encouragement system of claim 1, wherein determining whether to adjust the environmental content comprises determining whether to adjust the environmental content using a machine learning algorithm that receives the observation data as an input.

3. The user encouragement system of claim 1, wherein the controller includes further logic that when executed causes the user encouragement system to perform additional operations including:
generating a user model of the user with another machine learning classifier that classifies how the user is expected to react to the different types of the environmental content; and
updating the user model based upon the user reaction observed in response to presenting the environmental content.

4. The user encouragement system of claim 3, wherein the controller includes further logic that when executed causes the user encouragement system to perform additional operations including:
selecting other environmental content to test the user reaction to the other environmental content;
presenting the other environmental content to the user with the sensory immersion equipment; and
updating the user model based upon the user reaction observed in response to presenting the other environmental content, wherein the user is not explicitly informed that the other environmental content has been selected to test the user and refine the user model.

5. The user encouragement system of claim 1, wherein the at least one sensor comprises a camera.

6. The user encouragement system of claim 5, wherein the at least one sensor further comprises a body wearable device capable of measuring at least one of a body temperature, a pulse rate, or an electrocardiogram.

7. The user encouragement system of claim 1, wherein the observation system is communicatively coupled to a personal or desktop computing device of the user to monitor input/output signals of the personal or desktop computing device and wherein generating the observation data based upon the user reaction comprises generating the observation data based upon the input/output signals.

8. The user encouragement system of claim 1, wherein the at least one environmental display comprises one of a wallpaper-like display disposed on a wall or a table surface, a display panel, or a tiled array of display panels.

9. The user encouragement system of claim 1, wherein determining the influencing directive for encouraging the user towards the selected mental or emotional state comprises receiving an explicit directive.

10. The user encouragement system of claim 1, wherein determining the influencing directive for encouraging the user towards the selected mental or emotional state comprises executing the machine learning classifier to determine an implicit directive based upon observing the one or more activities performed by the user with the observation system.

11. The user encouragement system of claim 1, wherein selecting the environmental content from the plurality of different types of the environmental content comprises:
selecting a first portion of the environmental content from a generic library including first content that has been curated for a generic class of people into which the user is categorized; and
selecting a second portion of the environmental content from a custom library including second content that has been curated specifically for the user based upon previous interactions of the user with the user encouragement system.

12. At least one non-transitory machine-accessible storage medium that provides instructions that, when executed by one or more machines, will cause the one or more machines to perform operations comprising:
determining an influencing directive, wherein determining the influencing directive includes:
monitoring one or more activities performed by a user;
identifying the one or more activities; and
determining a selected mental or emotional state that is conducive to the user accomplishing the one or more activities identified;
selecting environmental content, based upon the influencing directive, from a plurality of different types of environmental content;
presenting the environmental content to alter an ambience of a room via sensory immersion equipment, the sensory immersion equipment including at least one environmental display and a personal display for a personal or desktop computing device, wherein the at least one environmental display includes an electronic display viewable from within the room, larger than the personal display, and which fills at least 110 degrees of vision of the user within the room;

adjusting a first theme of an application displayed on the personal display to conform with a second theme displayed on the environmental display;

generating observation data based upon observing a user reaction to the environmental content with the observation system, the observation system including at least one sensor capable of observing the user reaction; and determining whether to adjust the environmental content based upon the observation data with a goal of advancing the user towards the selected mental or emotional state.

13. The at least one non-transitory machine-accessible storage medium of claim 12, wherein determining whether to adjust the environmental content comprises determining whether to adjust the environmental content using a machine learning algorithm that receives the observation data as an input.

14. The at least one non-transitory machine-accessible storage medium of claim 12, further providing instructions that, when executed by the one or more machines, will cause the one or more machines to perform further operations, comprising:

generating a user model of the user with another machine learning classifier that classifies how the user is expected to react to the different types of the environmental content; and updating the user model based upon the user reaction observed in response to presenting the environmental content.

15. The at least one non-transitory machine-accessible storage medium of claim 14, further providing instructions that, when executed by the one or more machines, will cause the one or more machines to perform further operations, comprising:

selecting other environmental content to test the user reaction to the other environmental content;

presenting the other environmental content to the user with the sensory immersion equipment; and updating the user model based upon the user reaction observed in response to presenting the other environmental content, wherein the user is not explicitly informed that the other environmental content has been selected to test the user and refine the user model.

16. The at least one non-transitory machine-accessible storage medium of claim 12, wherein generating observation data based upon observing the user reaction comprises:

generating the observation data based upon input/output signals of a personal or desktop computing device communicatively coupled to the observation system.

17. The at least one non-transitory machine-accessible storage medium of claim 12, wherein determining the influencing directive for encouraging the user towards the selected mental or emotional state comprises receiving an explicit directive.

18. The at least one non-transitory machine-accessible storage medium of claim 12, wherein determining the influencing directive for encouraging the user towards the selected mental or emotional state comprises executing the machine learning algorithm to determine an implicit directive based upon observing the one or more activities with the observation system.

19. A method of encouraging a user towards a selected mental or emotional state, comprising:

determining an influencing directive, wherein determining the influencing directive includes:

monitoring one or more activities performed by the user with an observation system;

identifying the one or more activities with a machine learning classifier; and determining a selected mental or emotional state that is conducive to the user accomplishing the one or more activities identified by the machine learning classifier;

selecting environmental content, based upon the influencing directive, from a plurality of different types of environmental content, wherein selecting the environmental content includes:

selecting a first portion of the environmental content from a generic library including first content that has been curated for a generic class of people into which the user is categorized; and selecting a second portion of the environmental content from a custom library including second content that has been curated specifically for the user based upon previous interactions of the user with the user encouragement system;

presenting the environmental content to the user via sensory immersion equipment that includes at least one environmental display for altering an ambience of a room, wherein the at least one environmental display is an electronic display;

generating observation data based upon observing a user reaction to the environmental content with the observation system, the observation system including at least one sensor capable of observing the user reaction; and determining whether to adjust the environmental content based upon the observation data with a goal of advancing the user towards the selected mental or emotional state.

* * * * *